(12) United States Patent
Komatsu et al.

(10) Patent No.: US 10,301,238 B2
(45) Date of Patent: May 28, 2019

(54) PROCESS FOR PRODUCING 2-CHLORO-3,3,3-TRIFLUOROPROPENE

(71) Applicant: DAIKIN INDUSTRIES, LTD., Osaka (JP)

(72) Inventors: Yuzo Komatsu, Osaka (JP); Masayuki Kishimoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/618,259

(22) Filed: Jun. 9, 2017

(65) Prior Publication Data

US 2017/0275220 A1  Sep. 28, 2017

Related U.S. Application Data

(63) Continuation of application No. 14/348,705, filed as application No. PCT/JP2012/077821 on Oct. 23, 2012.

(60) Provisional application No. 61/605,841, filed on Mar. 2, 2012, provisional application No. 61/570,927, filed on Dec. 15, 2011, provisional application No. 61/553,523, filed on Oct. 31, 2011.

(51) Int. Cl.
  *C07C 17/20* (2006.01)
  *C07C 17/25* (2006.01)
  *C07C 21/18* (2006.01)

(52) U.S. Cl.
  CPC .......... *C07C 17/25* (2013.01); *C07C 17/206* (2013.01)

(58) Field of Classification Search
  CPC .............................. C07C 17/206; C07C 17/25
  See application file for complete search history.

(56) References Cited

U.S. PATENT DOCUMENTS

| 5,811,603 A | 9/1998 | Elsheikh |
| 6,403,847 B1 | 6/2002 | Nakada et al. |
| 7,795,480 B2 | 9/2010 | Merkel et al. |
| 9,162,945 B2 * | 10/2015 | Kishimoto ............ C07C 17/206 |
| 2009/0030247 A1 | 1/2009 | Johnson et al. |
| 2009/0240090 A1 | 9/2009 | Merkel et al. |
| 2011/0155942 A1 | 6/2011 | Pigamo et al. |
| 2011/0207975 A9 | 8/2011 | Merkel et al. |
| 2014/0256995 A1 | 9/2014 | Wang et al. |

FOREIGN PATENT DOCUMENTS

| CN | 103946197 | 7/2014 | |
| JP | 2009-227675 | 10/2009 | |
| WO | 93/25507 | 12/1993 | |
| WO | 03/002251 | 1/2003 | |
| WO | 2007/079431 | 7/2007 | |
| WO | 2008/054781 | 5/2008 | |
| WO | 2009/003084 | 12/2008 | |
| WO | WO-2009015317 A1 * | 1/2009 | ........... C07C 17/206 |
| WO | 2009/158321 | 12/2009 | |
| WO | 2011/077394 | 6/2011 | |
| WO | 2012/052797 | 4/2012 | |
| WO | 2012/052798 | 4/2012 | |
| WO | 2012/098420 | 7/2012 | |

OTHER PUBLICATIONS

International Search Report dated Feb. 6, 2013 in International (PCT) Application No. PCT/JP2012/077821.
Written Opinion of the International Searching Authority dated Feb. 6, 2013 in International (PCT) Application No. PCT/JP2012/077821.
Chinese Office Action dated Feb. 2, 2015 in corresponding Chinese Application No. 201280053593.7 and English translation thereof.

\* cited by examiner

*Primary Examiner* — Medhanit W Bahta
(74) *Attorney, Agent, or Firm* — Wenderoth, Lind & Ponack, L.L.P.

(57) ABSTRACT

This invention provides a process for producing 2-chloro-3,3,3-trifluoropropene, comprising: reacting anhydrous hydrogen fluoride with at least one chlorine-containing compound selected from the group consisting of chloropropanes and chloropropenes represented by specific formulas in a gas phase in the presence of a chromium atom-containing fluorination catalyst while heating, the reaction being carried out in the presence of molecular chlorine or with a water content in the reaction system of 300 ppm or less. This invention enables suppression of catalyst deterioration and efficient production of 2-chloro-3,3,3-trifluoropropene in a simple and economically advantageous manner on an industrial scale.

20 Claims, No Drawings

PROCESS FOR PRODUCING 2-CHLORO-3,3,3-TRIFLUOROPROPENE

TECHNICAL FIELD

The present invention relates to a process for producing 2-chloro-3,3,3-trifluoropropene.

BACKGROUND ART

2-Chloro-3,3,3-trifluoropropene (HCFO-1233xf) represented by the chemical formula: $CF_3CCl=CH_2$ is a useful compound as an intermediate for producing various fluorocarbons, and also as a monomer component for various kinds of polymers.

A known process for producing 2-chloro-3,3,3-trifluoropropene (HCFO-1233xf) comprises reacting anhydrous hydrogen fluoride (HF) in a gas phase in the presence of a catalyst. For example, Patent Literature 1 listed below discloses a process comprising fluorination of 1,1,2,3-tetrachloropropene (HCO-1230xa) in a gas phase in the presence of a chromium-based catalyst. Patent Literature 2 listed below also reports a process in which HCO-1230xa is fluorinated in a gas phase, using a chromium-based catalyst.

However, the processes disclosed in the above literature are problematic in that since catalytic activity tends to deteriorate as a reaction proceeds, if the reaction is continued for a long period of time, catalytic activity decreases, resulting in decline in the selectivity of 2-chloro-3,3,3-trifluoropropene (HCFO-1233xf).

For example, Patent Literature 3 listed below discloses a process for preparing 2,3,3,3-tetrafluoropropene (HFO-1234yf) by using 1,1,2,3-tetrachloropropene (HCO-1230xa), 1,1,1,2,3-pentachloropropane (HCC-240db), or the like as a starting material, fluorinating the starting material with HF to produce 2-chloro-3,3,3-trifluoropropene (HCFO-1233xf), and then adding HF to the thus-obtained HCFO-1233xf to produce 2-chloro-1,1,1,2-tetrafluoropropane (HCFC-244bb), followed by a dehydrochlorination reaction. In this process, decline in catalytic activity as the reaction proceeds is also unavoidable in a first step, which comprises fluorinating HCO-1230xa, HCC-240db, or the like with HF in the presence of a fluorination catalyst such as a fluorinated chromium oxide to produce HCFO-1233xf. For example, Example 1 of Patent Literature 3, which describes a step of preparing HCFO-1233xf by reacting HCO-1230xa as a starting material with HF in the presence of fluorinated $Cr_2O_3$, discloses that the selectivity of HCFO-1233xf was decreased to about 83% after 650 hours of reaction time, and that the reaction was stopped due to loss of catalytic activity.

Patent Literature 4 listed below discloses a process comprising fluorination of 1,1,2,3-tetrachloropropene (HCO-1230xa), 1,1,1,2,3-pentachloropropane (HCC-240db), 2,3,3,3-tetrachloropropene (HCO-1230xf), or the like in the presence of a fluorination catalyst, in which catalyst deterioration is suppressed by adding an amine-based stabilizer, hydroquinone-based stabilizer, or other stabilizers.

However, according to this process, selectivity is decreased, and a satisfactory effect of suppressing decrease in catalytic activity cannot be attained. Thus, a periodic catalyst activation treatment is inevitable.

Patent Literature 5 listed below discloses a process in which 1,1,2,3-tetrachloropropene (HCO-1230xa) is reacted with HF in a liquid phase in the presence of an antimony halide catalyst. However, in addition to the difficulty in handling the catalyst, this process is not economical due to the occurrence of reactor corrosion, the necessity of waste treatment, and the like. Thus, the process is not suitable as an industrial production process. Furthermore, Patent Literature 6 listed below reports that 2-chloro-3,3,3-trifluoropropene (HCFO-1233xf) can be produced by reacting HCO-1230xa with HF in a liquid phase under catalyst-free conditions. However, because it requires a long reaction time due to a slow reaction rate; a large excess of HF; severe reaction conditions under high pressure; etc., this process is not suitable as an industrial scale production process.

As described above, a process for continuously producing 2-chloro-3,3,3-trifluoropropene (HCFO-1233xf) at a high yield in a simple and economical manner has not yet been established.

CITATION LIST

Patent Literature

PTL 1: WO 2007/079431
PTL 2: WO 2008/054781
PTL 3: Japanese Unexamined Patent Publication No. 2009-227675
PTL 4: U.S. Pat. No. 7,795,480
PTL 5: US 2009/0030247 A1
PTL 6: WO 2009/003084 A1

SUMMARY OF INVENTION

Technical Problem

The present invention has been accomplished in view of the foregoing state of the art, and its primary object is to provide a process for efficiently producing 2-chloro-3,3,3-trifluoropropene in a simple and economically advantageous manner even on an industrial scale.

Solution to Problem

The present inventors conducted extensive research to achieve the above object. As a result, the inventors found that in a process for producing 2-chloro-3,3,3-trifluoropropene by using a chloropropane compound or a chloropropene compound represented by a specific formula as a starting material and reacting the starting material with hydrogen fluoride in a gas phase in the presence of a chromium atom-containing fluorination catalyst while heating, decrease in catalytic activity can be suppressed when the reaction is conducted in the presence of molecular chlorine or when the water content in the reaction system is controlled at a very low concentration. In particular, the inventors found that when the reaction is conducted in the presence of molecular chlorine and the water content in the reaction system is controlled at a low concentration, decrease in catalytic activity can be suppressed over a long period of time, and 2-chloro-3,3,3-trifluoropropene can be continuously produced at a high yield for a long period of time. The present invention has been accomplished based on these findings.

More specifically, the present invention provides the following process for producing 2-chloro-3,3,3-trifluoropropene.

Item 1. A process for producing 2-chloro-3,3,3-trifluoropropene, comprising:

reacting anhydrous hydrogen fluoride with at least one chlorine-containing compound in a gas phase in the presence of a chromium atom-containing fluorination catalyst while heating, the at least one chlorine-containing compound being selected from the group consisting of chloropropanes represented by Formula (1): $CXYZCHClCH_2A$, wherein X, Y, and Z are the same or different and each is F or Cl, and A is a halogen atom, chloropropenes represented by Formula (2): $CXYZCCl=CH_2$, wherein X, Y, and Z are the same or different and each is F or Cl, and chloropropenes represented by Formula (3): $CXY=CClCH_2A$, wherein X and Y are the same or different and each is F or Cl, and A is a halogen atom, and the reaction being carried out in the presence of molecular chlorine.

Item 2. A process for producing 2-chloro-3,3,3-trifluoropropene, comprising:

reacting anhydrous hydrogen fluoride with at least one chlorine-containing compound in a gas phase in the presence of a chromium atom-containing fluorination catalyst while heating, the at least one chlorine-containing compound being selected from the group consisting of chloropropanes represented by Formula (1): $CXYZCHClCH_2A$, wherein X, Y, and Z are the same or different and each is F or Cl, and A is a halogen atom, chloropropenes represented by Formula (2): $CXYZCCl=CH_2$, wherein X, Y, and Z are the same or different and each is F or Cl, and chloropropenes represented by Formula (3): $CXY=CClCH_2A$, wherein X and Y are the same or different and each is F or Cl, and A is a halogen atom, and the reaction being carried out with a water content in the reaction system of 300 ppm or less based on the total weight of the at least one chlorine-containing compound used as a starting material.

Item 3. A process for producing 2-chloro-3,3,3-trifluoropropene, comprising:

reacting anhydrous hydrogen fluoride with at least one chlorine-containing compound in a gas phase in the presence of a chromium atom-containing fluorination catalyst while heating, the at least one chlorine-containing compound being selected from the group consisting of chloropropanes represented by Formula (1): $CXYZCHClCH_2A$, wherein X, Y, and Z are the same or different and each is F or Cl, and A is a halogen atom, chloropropenes represented by Formula (2): $CXYZCCl=CH_2$, wherein X, Y, and Z are the same or different and each is F or Cl, and chloropropenes represented by Formula (3): $CXY=CClCH_2A$, wherein X and Y are the same or different and each is F or Cl, and A is a halogen atom, and the reaction being carried out in the presence of molecular chlorine and with a water content in the reaction system of 300 ppm or less based on the total weight of the at least one chlorine-containing compound used as a starting material.

Item 4. The process according to Item 1 or 3, wherein the amount of molecular chlorine supplied is 0.001 to 0.3 moles per mole of the at least one chlorine-containing compound used as a starting material.

Item 5. The process according to Item 4, wherein the at least one chlorine-containing compound used as a starting material is selected from the group consisting of chloropropenes represented by Formula (2): $CXYZCCl=CH_2$, wherein X, Y, and Z are the same as above, and chloropropenes represented by Formula (3): $CXY=CClCH_2A$, wherein X, Y, and A are the same as above, and the amount of molecular chlorine supplied is 0.001 to 0.2 moles per mole of the at least one chlorine-containing compound.

Item 6. The process according to Item 2 or 3, wherein the reaction is carried out with a water content in the reaction system of 100 ppm or less based on the total weight of the at least one chlorine-containing compound used as a starting material.

Item 7. The process according to any one of Items 1 to 6, wherein the chromium atom-containing fluorination catalyst is at least one catalyst selected from the group consisting of chromium oxides and fluorinated chromium oxides.

Item 8. The process according to Item 7, wherein the fluorination catalyst is at least one catalyst selected from the group consisting of chromium oxides represented by the composition formula: $CrO_m$ (1.5<m<3) and fluorinated chromium oxides obtained by fluorinating the chromium oxides.

Item 9. The process according to any one of Items 1 to 8, wherein the reaction is carried out at a temperature in the range of 200 to 380° C.

Item 10. The process according to any one of Items 1 to 9, wherein the reaction is carried out using 3 moles or more of anhydrous hydrogen fluoride per mole of the at least one chlorine-containing compound used as a starting material.

Item 11. The process according to any one of Items 1 to 10, wherein the at least one chlorine-containing compound used as a starting material is selected from the group consisting of 1,1,1,2,3-pentachloropropane and 1,1,2,3-tetrachloropropene.

Hereinafter, the process for producing 2-chloro-3,3,3-trifluoropropene of the present invention is specifically described.

(I) Starting Compound

In the present invention, used as a starting material is at least one chlorine-containing compound selected from the group consisting of chloropropanes represented by Formula (1): $CXYZCHClCH_2A$, wherein X, Y, and Z are the same or different and each is F or Cl, and A is a halogen atom, chloropropenes represented by Formula (2): $CXYZCCl=CH_2$, wherein X, Y, and Z are the same or different and each is F or Cl, and chloropropenes represented by Formula (3): $CXY=CClCH_2A$, wherein X and Y are the same or different and each is F or Cl, and A is a halogen atom. Examples of the halogen atom represented by A in Formulas (1) and (3) above include F, Cl, Br, and I.

When these chlorine-containing compounds are used as a starting material and reacted with anhydrous hydrogen fluoride according to the below-described conditions, the desired 2-chloro-3,3,3-trifluoropropene (HCFO-1233xf) can be continuously produced for a long period of time at a high yield in a single-step reaction.

Among the starting compounds, specific examples of the chloropropanes represented by Formula (1): $CXYZCHClCH_2A$ include 1,1,1,2,3-pentachloropropane ($CCl_=CHClCH_2Cl$) (HCC-240db), 1-fluoro-1,1,2,3-tetrachloropropane ($CFCl_2CHClCH_2Cl$) (HCFC241db), 1,1-difluoro-1,2,3-trichloropropane ($CF_2ClCHClCH_2Cl$) (HCFC-242dc), and 2,3-dichloro-1,1,1-trifluoropropane ($CF_3CHClCH_2Cl$) (HCFC-243db). Specific examples of the chloropropenes represented by Formula (2): $CXYZCCl=CH_2$ include 2,3,3,3-tetrachloropropene ($CCl_3CCl=CH_2$) (HCO-1230xf) and 2,3-dichloro-3,3-difluoropropene ($CF_2ClCCl=CH_2$) (HCFO-1232xf). Specific examples of the chloropropenes represented by Formula (3): $CXY=CClCH_2A$ include 1,1,2,3-tetrachloropropene ($CCl_2=CClCH_2Cl$) (HCO-1230xa).

All of these starting compounds are known compounds that can be easily obtained.

in the present invention, the starting compounds can be used singly, or in a combination of two or more.

(II) Reaction Process

The production process of the present invention is a process that comprises reacting at least one of the above-described starting compounds with anhydrous hydrogen fluoride in a gas phase in the presence of a chromium atom-containing fluorination catalyst while heating, the reaction being conducted in the presence of molecular chlorine or with a water content in the reaction system of 300 ppm or less based on the total weight of the at least one chlorine-containing compound used as a starting material.

When the starting compound is reacted with anhydrous hydrogen fluoride under such conditions, the desired 2-chloro-3,3,3-trifluoropropene (HCFO-1233xf) can be obtained with high selectivity in a single-step reaction. Further, decrease in catalytic activity is suppressed, and HCFO-1233xf can be continuously produced for a long period of time with high selectivity and a high yield. Accordingly, the production process of the present invention is very useful as a process for producing HCFO-1233xf on an industrial scale.

Hereinafter, the process in which the reaction is conducted in the presence of molecular chlorine, and the process in which the water content is controlled are specifically described.

(i) Process in which the Reaction is Conducted in the Presence of Molecular Chlorine:

A first aspect of the present invention is a process in which the reaction is conducted in the presence of molecular chlorine. In this process, when the aforementioned starting compound is reacted with hydrogen fluoride in a gas phase, using a chromium atom-containing fluorination catalyst as a catalyst, the reaction is conducted in the presence of molecular chlorine.

In this case, in the process in which the reaction is conducted in a gas phase, the starting compound may be in a liquid form when supplied as long as the starting compound is in a gaseous form when it comes into contact with anhydrous hydrogen. fluoride within the reaction temperature range described below. For example, when the starting compound is liquid at an ordinary temperature and ordinary pressure, the starting compound is vaporized using a vaporizer (vaporization region), passed through a preheating region, and then supplied to a mixing region wherein the starting compound is contacted with anhydrous hydrogen fluoride, whereby the reaction can be conducted in a gas phase. The reaction may also be carried out by supplying the starting compound in a liquid form to a reactor, heating a catalyst layer placed in the reactor to the vaporization temperature or higher of the starting compound, and vaporizing the starting compound when the compound enters a reaction range to react with hydrogen fluoride.

The reaction may be generally conducted by supplying anhydrous hydrogen fluoride to a reactor in a gas phase together with the starting compound. The amount of anhydrous hydrogen fluoride to be used is not particularly limited. To achieve high selectivity of 2-chloro-3,3,3-trifluoropropene (HCFO-1233xf), the amount of anhydrous hydrogen fluoride is preferably about 3 moles or more, and more preferably about 8 moles or more, per mole of the chlorine-containing compound used as a starting material. When the amount of anhydrous hydrogen fluoride is less than this range, the selectivity of HCFO-1233xf and catalytic activity tend to decrease. Thus, an amount of anhydrous hydrogen fluoride less than the above range is unfavorable.

The upper limit of the amount of anhydrous hydrogen fluoride is not particularly limited. Even if the amount of hydrogen fluoride is excessively large, there is less influence on the selectivity and conversion. However, the productivity is decreased because of increase in the amount of hydrogen fluoride to be separated during purification. For this reason, the amount of anhydrous hydrogen fluoride is generally preferably about 100 moles or less and more preferably about 50 moles or less, per mole of the chlorine-containing compound used as a starting material.

In the production process of the present invention, the chlorine-containing compound used as a starting material is reacted with anhydrous hydrogen fluoride, using a chromium atom-containing fluorination catalyst as a catalyst, in the presence of molecular chlorine according to the below-described conditions. This process enables decrease in catalytic activity to be suppressed, and the selectivity of 2-chloro-3,3,3-trifluoropropene (HCFO-1233xf) to be maintained at a high value.

Examples of usable chromium atom-containing fluorination catalysts include halides and oxides. Of them, as examples of preferred catalysts, $CrCl_3$, $CrF_3$, $Cr_2O_3$, $CrO_2$, $CrO_3$, and the like can be mentioned. These catalysts may be supported on a carrier. There is no particular limitation on the carrier, and examples of the carrier include porous alumina silicates typified by zeolites, aluminum oxides, silicon oxides, activated carbons, titanium oxides, zirconia oxides, zinc oxides, and aluminum fluorides.

In the present invention, it is particularly preferable to use at least one catalyst selected from the group consisting of chromium oxides and fluorinated chromium oxides. Examples of such chromium oxides and fluorinated chromium oxides include crystalline chromium oxides, amorphous chromium oxides, and fluorinated products thereof.

There is no particular limitation on the composition of the chromium oxides. For example, the chromium oxides are oxides represented by the composition formula: $CrO_m$, wherein m is preferably in the range of $1.5<m<3$ and more preferably $2<m<2.75$. Chromium oxide catalysts in any form, such as powder form and pellet form may be used, as long as they are suitable for the reaction. Of them, chromium oxide catalysts in the form of pellets are preferable. The above-mentioned chromium oxide catalysts can be produced, for example, by the process disclosed in Japanese Unexamined Patent Publication No. H5-146680.

The fluorinated chromium oxides can be prepared, for example, by fluorinating the chromium oxides obtained by the above-described process with hydrogen fluoride (HF treatment). The fluorination temperature may be, for example, about 100 to about 460° C. For instance, the fluorination of a chromium oxide may be carried out by supplying anhydrous hydrogen fluoride to a reactor in which the chromium oxide is placed. After the chromium oxide is fluorinated in this manner, the starting material is supplied to the reactor, thereby allowing the reaction for producing the desired product to proceed efficiently.

Since the reaction is carried out in the presence of hydrogen fluoride in the process of the present invention, even in the case where a chromium oxide is not fluorinated in advance, the fluorination of catalyst will proceed during the reaction.

The degree of fluorination is not particularly limited. For example, a chromium oxide having a fluorine content of about 5 to about 30 wt % may be suitably used.

The surface area of the catalyst is varied as a result of the fluorination treatment. In general, the greater the specific surface area, the higher the activity. The specific surface area of chromium oxide after fluorination is preferably about 25 to about 130 $m^2/g$, but is not limited to this range.

further, the catalyst disclosed in Japanese Unexamined Patent Publication No. H11-171806, which comprises, as a main component, a chromium compound containing at least one metallic element selected from the group consisting of indium, gallium, cobalt, nickel, zinc, and aluminum, may be used as a chromium oxide catalyst or a fluorinated chromium oxide catalyst.

There is no particular limitation on the method of using the catalyst. The catalyst may be used so that the starting material gases are sufficiently brought into contact with the catalyst. For example, a method of forming a catalyst layer by immobilizing a catalyst in a reactor, a method of dispersing a catalyst in a fluidized bed, or other methods can be employed.

The production process of the present invention requires the reaction to be conducted in the presence of molecular chlorine when the chlorine-containing compound is reacted with anhydrous hydrogen fluoride, using the above catalyst. Conducting the reaction in the presence of molecular chlorine makes it possible to suppress decrease in catalytic activity and to continuously produce 2-chloro-3,3,3-trifluoropropene (HCFO-1233xf) with high selectivity for a long period of time.

There is no particular limitation on the process in which the reaction is conducted in the presence of molecular chlorine. The reaction may be generally conducted by supplying molecular chlorine to a reactor together with the chlorine-containing compound used as a starting material. Alternatively, molecular chlorine may also be supplied to a reactor after being dissolved in the chlorine-containing compound.

The amount of molecular chlorine supplied is preferably about 0.001 to about 0.3 moles, more preferably about 0.001 to about 0.05 moles, and particularly preferably about 0.002 to about 0.03 moles, per mole of the chlorine-containing compound used as a starting material. In the case where at least one chlorine-containing compound selected from the group consisting of chloropropenes represented by Formula (2): $CXYZCCl\!=\!CH_2$ and chloropropenes represented by Formula (3): $CXY\!=\!CClCH_2A$ is used as a starting material, in order to more effectively suppress decrease in catalytic activity, the amount of molecular chlorine supplied is preferably about 0.001 to about 0.2 moles, and more preferably about 0.001 to about 0.1 moles, per mole of the chlorine-containing compound used as a starting material.

If the amount of molecular chlorine supplied is excessively small, the effect of suppressing decrease in catalytic activity cannot be sufficiently attained; whereas if the amount of molecular chlorine supplied is excessively large, polychlorinated products, such as 1,2-dichloro-3,3,3-trifluoropropene, are increased, resulting in decline in the selectivity of 2-chloro-3,3,3-trifluoropropene (HCFC-1233xf). Thus, an excessively small or large amount of molecular chlorine is not desirable.

As one specific embodiment of the process of the present invention, a process can be mentioned in which a fluorination catalyst is placed into a tubular flow reactor, and the above-mentioned chlorine-containing compound used as a starting material, anhydrous hydrogen fluoride, and molecular chlorine are introduced to the reactor.

The reactor used is preferably made of a material resistant to the corrosive action of hydrogen fluoride, such as Hastelloy, Inconel, Monel, or the like.

The starting material may be supplied to the reactor as is; or a gas that is inert to the starting material and catalyst, such as nitrogen, helium, and argon, may coexist. The concentration of the inert gas is about 0 to about 80 mol % based on the amount of the gaseous components introduced into the reactor, i.e., the amount of the chlorine-containing compound, anhydrous hydrogen fluoride, and chlorine gas plus the amount of the inert gas.

Moreover, in the process of the present invention, oxygen may be supplied at the same time chlorine is supplied. By doing so, decrease in catalytic activity can be further suppressed. The amount of oxygen supplied is not particularly limited and is preferably about 0.001 to about 0.5 moles, per mole of the chlorine-containing compound used as a starting material.

the lower limit of the reaction temperature is not particularly limited because the lower reaction temperature is advantageous in terms of less decomposition of the starting material and product. However, if the temperature is excessively low, a chlorine-containing compound conversion tends to decrease. For this reason, the reaction temperature is preferably 200° C. or more, and more preferably 220° C. or more.

Regarding the upper limit of the reaction temperature, an excessively high reaction temperature is not preferable because an excessively high reaction temperature notably decreases catalytic activity due to decomposition of the starting material; and easily causes formation of $C_1$, $C_2$ compounds, $CF_3CH\!=\!CHF$, and isomers, such as $CF_3CH\!=\!CHCl$, as by-products. For this reason, the reaction temperature is preferably 380° C. or less, and more preferably 350° C. or less.

Note that in the case where only oxygen is used for catalytic activation without using chlorine, the activation effect is difficult to obtain at a reaction temperature of less than 300° C., and thus the reaction temperature needs to be increased; additionally, even if the reaction temperature is increased to about 350° C., the amount of oxygen required for the activation becomes large, causing unfavorable effects such as the necessity of dealing with combustible gas.

The pressure during the reaction is not particularly limited, and the reaction may be conducted under reduced pressure, ordinary pressure, or increased pressure. Although the reaction may be generally carried out at pressure near atmospheric pressure (0.1 MPa), it can also proceed smoothly under reduced pressure of less than 0.1 MPa. Furthermore, the reaction may be conducted under increased pressure within a range in which the starting material does not liquefy.

There is no limitation on the contact time. For example, the contact time, which is represented by $W/F_0$, is preferably adjusted to about 0.5 to about 70 g·sec/mL, and more preferably about 1 to about 50 g·sec/mL. $W/F_0$ is the ratio of the amount of catalyst used W(g) to the total flow rate $F_0$ (flow rate at 0° C., 0.1 MPa: mL/sec) of the starting material gases supplied to the reaction system. The total flow rate of the starting material gases in this case refers to the total flow rate of the chlorine-containing compound, anhydrous hydrogen fluoride, and chlorine. In the case where an inert gas, oxygen, or other gases are further used, the total flow rate of the starting material gases refers to the total flow rate of the chlorine-containing compound, anhydrous hydrogen fluoride, and chlorine plus the flow rate of the inert gas, oxygen, or other gases.

In the production process of the present invention, other compounds may be present in the reaction system within a range that satisfies the above-described conditions, as long as they do not adversely affect the effects of the present invention.

For example, the known stabilizers disclosed in Patent Literature 4 (U.S. Pat. No. 7,795,480) described above, such as an amine-based stabilizer and hydroquinone-based stabilizer, may be present in the reaction system.

(ii) Process in which the Water Content in the Reaction System is Controlled:

A second aspect of the present invention is a process in which the water content in the reaction system is controlled. In this process, when the aforementioned chlorine-containing compound as a starting material is reacted with hydrogen fluoride in a gas phase, using a chromium atom-containing fluorination catalyst as a catalyst, the water content in the reaction system is controlled at a small amount.

The type of catalyst to be used, specific reaction process, reaction conditions, and the like may be the same as in the above-described case in which the reaction is conducted in the presence of molecular chlorine. Each component, such as oxygen, inert gas and stabilizer, is also usable in the same conditions as in the case in which the reaction is conducted in the presence of molecular chlorine. By controlling the water content in the reaction system at a small amount, decrease in catalytic activity can be suppressed in the same reaction temperature range as in the case in which the reaction is conducted in the presence of molecular chlorine.

In the process in which the water content in the reaction system is controlled, it is necessary for the water content in the reaction system when the starting compound and hydrogen fluoride are reacted in a gas phase to be 300 ppm or less, preferably 100 ppm or less, based on the weight of the chlorine-containing compound used as a starting material. A water content exceeding this range deactivates the catalyst and increases the intermediate products HCFO-1232xf and HCO-1230xa; thus, it is not preferable in continuous production.

The water content in the reaction system refers to the water content present when the chlorine-containing compound and anhydrous hydrogen fluoride contact the catalyst and undergo reaction; i.e., the water content of the chlorine-containing compound used as a starting material and anhydrous hydrogen fluoride, plus the water content of components added as necessary, such as oxygen, inert gas, and stabilizer.

There is no particular limitation on the method of decreasing the water content in the reaction system. The chlorine-containing compound used as a starting material, hydrogen fluoride, and other additional components may be dehydrated by a known method prior to the reaction. A method of supplying the previously dehydrated materials to the reaction; a method of dehydrating the starting material, hydrogen fluoride, and other additional components, and subsequently supplying them to the reaction system; or other methods can be suitably employed.

As the method of dehydrating the chlorine-containing compound used as a starting material, for example, a distillation method or a method using a dehydrating agent may be employed, and a method of removing water using a dehydrating agent is preferable in terms of efficiency. As the method of removing water using a dehydrating agent, for example, a method of adsorbing water using a zeolite is preferable. The form of zeolite is not particularly limited, and a zeolite in the form of powder, granules, or pellets may be used. Regarding the pore size of zeolite, a zeolite having a pore size of about 2.0 to about 6.0 Å may be used. There is no particularly limitation on the method of bringing the chlorine-containing compound into contact with a zeolite, and it is generally preferable in terms of efficiency that the chlorine-containing compound in a gaseous form or liquid form is flowed into a container in which a zeolite is placed.

Moreover, the water content in the reaction system can also be decreased by a method in which a dehydrating agent packed bed is provided before a catalyst packed bed in a reactor (reaction tube) without separately providing a container containing a dehydrating agent, and the starting material supplied in the reactor (reaction tube) is passed through the dehydrating agent packed bed and then passed through the catalyst packed bed. The location of the dehydrating agent packed bed is not particularly limited, and the dehydrating agent packed bed is preferably disposed in a portion at 100° C. or less before the catalyst packed bed for the reason that a temperature exceeding 100° C. causes desorption of adsorbed water from the dehydrating agent.

As the method of dehydrating hydrogen fluoride, for example, a distillation method or other methods may be used.

Specific dehydration conditions may be determined by, for example, preliminarily conducting an experiment according to the water content of the starting material, additional components, etc., to be used; the type and structure of a device to be used; and other conditions so that the water content in the reaction system is adjusted to a desired value.

(iii) Process in which the Water Content is Controlled and the Reaction is Conducted in the Presence of Molecular Chlorine:

In the process for producing 2-chloro-3,3,3-trifluoropropene of the present invention, it is preferable that the reaction is conducted, in particular, in the presence of molecular chlorine and with a water content in the reaction system of 300 ppm or less based on the weight of the chlorine-containing compound used as a starting material. Reaction conditions in this case may be the same as those in (i) and (ii) described above.

The reaction of the chlorine-containing compound used as a starting material with hydrogen fluoride under these conditions enables, in particular, notable suppression of decrease in catalytic activity, as well as production of HCFO-1233xf with high selectivity and a high yield for a long period of time.

(III) Reaction Product

According to the above-mentioned processes of the present invention, the desired 2-chloro-3,3,3-trifluoropropene (HCFO-1233xf) can be obtained with high selectivity in a single-step reaction from at least one of the chlorine-containing compounds represented by Formulas (1) to (3), used as a starting material; additionally, in the case where the reaction continues, decrease in catalytic activity is slight, and high selectivity can be maintained for a long period of time.

In the process of the present invention, 2-chloro-3,3,3-trifluoropropene (HCFO-1233xf) can be separated and collected by distillation of the product obtained at the reactor outlet or by other methods.

1,1,1,2,2-pentafluoropropane (HFC-245cb), a main component of by-products contained in the product, can be easily converted to 2,3,3,3-tetrafluoropropene (HFO-1234yf) by dehydrofluorination reaction. Accordingly, 1,1,1,2,2-pentafluoropropane (HFC-245cb) and 2,3,3,3-tetrafluoropropene (HFO-1234yf) (which is regarded as a final object product), which are contained in the product, can also be used effectively as useful compounds.

Advantageous Effects of Invention

According to the process of the present invention, 2-chloro-3,3,3-trifluoropropene (HCFC-1233xf) can be produced at a high yield in a single-step reaction, using a chlorine-containing compound represented by a specific formula as a starting material; additionally, in the case where the reaction continues, decrease in catalytic activity is slight, and high selectivity can be maintained for a long period of time.

In particular, in the case where the reaction is conducted in the presence of molecular chlorine, and the water content is controlled at a small amount, decrease in catalytic activity can be suppressed, and HCFO-1233xf can be obtained with high selectivity and a high yield over a long period of time.

Accordingly, the process of the present invention enables 2-chloro-3,3,3-trifluoropropene (HCFC-1233xf) to be continuously produced at a high yield for a long period of time without requiring complicated treatments, such as catalyst replacement and catalyst regeneration treatment.

Therefore, the process of the present invention is a highly advantageous process as a process for producing 2-chloro-3,3,3-trifluoropropene (HCFC-1233xf) from an industrial standpoint.

DESCRIPTION OF EMBODIMENTS

Hereinafter, the present invention is described in more detail with reference to Examples.

EXAMPLE 1

10 g of a catalyst (fluorine content: about 15.0% by weight) obtained by fluorinating a chromium oxide represented by the composition formula: $CrO_2$ was placed into a tubular Hastelloy reactor with an inner diameter of 15 mm and a length of 1 m. The reactor was maintained at atmospheric pressure (0.1 MPa) and 250° C., and anhydrous hydrogen fluoride (HF) gas having a water content of 50 ppm was supplied to the reactor at a flow rate of 114 mL/min (flow rate at 0° C., 0.1 MPa) for 1 hour. $CCl_3CHClCH_2Cl$ (HCC-240db) having a water content of 40 ppm was then supplied at a flow rate of 5.6 mL/min (gas flow rate at 0° C., 0.1 MPa). The water content in the reaction system at this point based on the weight of HCC-240db was 134 ppm. The molar ratio of HF:HCC-240db was 20:1. The contact time ($W/F_0$) was 5.0 g·sec/cc.

The outlet gas from the reactor after 20 hours, 100 hours, and 200 hours was analyzed using gas chromatography. Table 1 shows the analysis results.

Under these conditions, the selectivity of HCFO-1233xf was maintained at a high value: 96.7% after 20 hours, and 93.9% after 200 hours. The rate of decline in the total selectivity of useful compounds of HCFO-1233xf, HFC-245cb, and HFO-1234yf was 0.37%/day; thus, the decline in the selectivity was suppressed.

TABLE 1

|  | Reaction Time (hr) | | |
| --- | --- | --- | --- |
|  | 20 | 100 | 200 |
| Conversion of HCC-240db (%) | 99.9 | 99.4 | 98.9 |
| Selectivity of HFO-1234yf (%) | 0.4 | 0.2 | 0.1 |
| Selectivity of HFC-245cb (%) | 0.9 | 0.2 | 0.0 |
| Selectivity of HCFO-1233xf (%) | 96.7 | 95.8 | 93.9 |
| Selectivity of HCFO-1232xf (%) | 0.3 | 0.9 | 1.3 |
| Selectivity of HCO-1230xa (%) | 0.2 | 0.7 | 1.1 |
| Others (%) | 1.5 | 2.2 | 3.6 |

Comparative Example 1

A reaction was conducted under the same conditions as in Example 1, except that $CCl_3CHClCH_2Cl$ (HCC-240db) having a water content of 250 ppm was supplied. The water content in the reaction system at this point based on the weight of HCC-240db was 340 ppm. Table 2 shows the analysis results of the outlet gas.

Under these conditions, the selectivity of HCFO-1233xf was 95.6% after 20 hours, and decreased to 89.8% after 200 hours. The total selectivity of useful compounds of HCFO-1233xf, HFC-245 cb, and HFO-1234yf was decreased at 0.77%/day.

TABLE 2

|  | Reaction time (hr) | | |
| --- | --- | --- | --- |
|  | 20 | 100 | 200 |
| Conversion of HCC-240db (%) | 99.8 | 99.2 | 98.0 |
| Selectivity of HFO-1234yf (%) | 0.2 | 0.1 | 0.0 |
| Selectivity of HFC-245cb (%) | 0.4 | 0.0 | 0.0 |
| Selectivity of HCFO-1233xf (%) | 95.6 | 92.9 | 89.8 |
| Selectivity of HCFO-1232xf (%) | 0.5 | 2.4 | 4.6 |
| Selectivity of HCO-1230xa (%) | 0.5 | 1.2 | 1.8 |
| Others (%) | 1.5 | 3.4 | 3.8 |

EXAMPLE 2

A reaction was carried out under the same conditions as in Example 1, except that $CCl_3CHClCH_2Cl$ (HCC-240db) in which 0.008 moles of molecular chlorine per mole of HCC-240db was dissolved was supplied. The water content in the reaction system at this point based on the weight of HCC-240db was 134 ppm. Table 3 shows the analysis results of the outlet gas.

Under these conditions, the selectivity of HCFO-1233xf was maintained at a high value: 96.1% after 20 hours, and 96.3% after 200 hours. The total selectivity of useful compounds of HCFO-1233xf, HFC-245cb, and HFO-1234yf had a decline rate of 0.03%/day, and was maintained at an almost constant value.

TABLE 3

|  | Reaction Time (hr) | | |
| --- | --- | --- | --- |
|  | 20 | 100 | 200 |
| Conversion of HCC-240db (%) | 99.9 | 100 | 99.9 |
| Selectivity of HFO-1234yf (%) | 0.3 | 0.3 | 0.2 |
| Selectivity of HFC-245cb (%) | 0.6 | 0.4 | 0.3 |
| Selectivity of HCFO-1233xf (%) | 96.1 | 96.2 | 96.3 |
| Selectivity of HCFO-1232xf (%) | 0.2 | 0.1 | 0.3 |
| Selectivity of HCO-1230xa (%) | 0.2 | 0.1 | 0.1 |
| Others (%) | 1.6 | 2.9 | 5.1 |

EXAMPLE 3

$CCl_3CHClCH_2Cl$ (HCC-240db) having a water content of 15 ppm was prepared by adding molecular sieves 4A (100 g) to HCC-240db (1 kg) having a water content of 40 ppm, which was used in Example 1, hermetically sealing the resulting mixture, and allowing the mixture to stand for 24 hours.

In addition, anhydrous hydrogen fluoride (HF) having a water content of 10 ppm was prepared by placing anhydrous hydrogen fluoride (HF) (800 g) having a water content of 50 ppm, which was used in Example 1, in a 1 polytetrafluoroethylene container equipped with a reflux condenser and a distillation tube, and heating the container to collect HF.

A reaction was carried out under the same conditions as in Example 1, except that $CCl_3CHClCH_2Cl$ (HCC-240db) having a water content of 15 ppm and anhydrous hydrogen fluoride (HF) gas having a water content of 10 ppm obtained in the above manner were supplied. The water content in the reaction system at this point based on the weight of HCC-240db was 34 ppm. Table 4 shows the analysis results of the outlet gas.

Under these conditions, the selectivity of HCFO-1233xf was maintained at a high value: 96.8% after 20 hours and 95.6% after 200 hours. The rate of decline in total selectivity of useful compounds of HCFO-1233xf, HFC-245cb, and HFO-1234yf was 0.24%/day; thus, the decline in the selectivity was suppressed.

TABLE 4

|  | Reaction Time (hr) | | |
| --- | --- | --- | --- |
|  | 20 | 100 | 200 |
| Conversion of HCC-240db (%) | 100 | 99.8 | 99.5 |
| Selectivity of HFO-1234yf (%) | 0.5 | 0.3 | 0.2 |
| Selectivity of HFC-245cb (%) | 0.7 | 0.6 | 0.4 |
| Selectivity of HCFO-1233xf (%) | 96.8 | 96.1 | 95.6 |
| Selectivity of HCFO-1232xf (%) | 0.3 | 0.6 | 1.0 |
| Selectivity of HCO-1230xa (%) | 0.2 | 0.5 | 0.8 |
| Others (%) | 1.5 | 1.9 | 2.0 |

EXAMPLE 4

A reaction was carried out under the same conditions as in Comparative Example 1, except that chlorine gas was supplied at 0.14 mL/min (gas flow rate at 0° C., 0.1 MPa) concurrently with supply of $CCl_3CHClCH_2Cl$ (HCC-240db). The water content in the reaction system at this point based on the weight of HCC-240db was 340 ppm. Table 5 shows the analysis results of the outlet gas.

Under these conditions, the selectivity of HCFO-1233xf was maintained at a high value: 96.2% after 20 hours, and 95.3% after 200 hours. The rate of decline in total selectivity of useful compounds of HCFO-1233xf, HFC-245cb, and HFO-1234yf was 0.11%/day; thus, the decline in the selectivity was suppressed.

TABLE 5

|  | Reaction Time (hr) | | |
| --- | --- | --- | --- |
|  | 20 | 100 | 200 |
| Conversion of HCC-240db (%) | 100 | 100 | 100 |
| Selectivity of HFO-1234yf (%) | 0.2 | 0.1 | 0.1 |
| Selectivity of HFC-245cb (%) | 0.3 | 0.2 | 0.2 |
| Selectivity of HCFO-1233xf (%) | 96.2 | 95.9 | 95.3 |
| Selectivity of HCFO-1232xf (%) | 0.1 | 0.2 | 0.3 |
| Selectivity of HCO-1230xa (%) | 0.0 | 0.1 | 0.2 |
| Others (%) | 3.2 | 3.4 | 3.9 |

EXAMPLE 5

A reaction was carried out under the same conditions as in Example 1, except that chlorine gas was supplied at 0.14 mL/min (gas flow rate at 0° C., 0.1 MPa) concurrently with supply of $CCl_3CHClCH_2Cl$ (HCC-240db). At this point, the molar ratio of $Cl_2$:HCC-240db was 0.025:1, and the water content in the reaction system based on the weight of HCC-240db was 134 ppm. Table 6 shows the analysis results of the outlet gas.

Under these conditions, the selectivity of HCFO-1233xf was maintained at a high value: 94.8% after 20 hours and 94.0% after 200 hours. The total selectivity of useful compounds of HCFO-1233xf, HFC-245cb, and HFO-1234yf had a decline rate of 0.09%/day, and was maintained at an almost constant value.

TABLE 6

|  | Reaction Time (hr) | | |
| --- | --- | --- | --- |
|  | 20 | 100 | 200 |
| Conversion of HCC-240db (%) | 100 | 100 | 100 |
| Selectivity of HFO-1234yf (%) | 0.3 | 0.2 | 0.1 |
| Selectivity of HFC-245cb (%) | 0.4 | 0.2 | 0.0 |
| Selectivity of HCFO-1233xf (%) | 94.8 | 94.5 | 94.0 |
| Selectivity of HCFO-1232xf (%) | 0.1 | 0.2 | 0.3 |
| Selectivity of HCO-1230xa (%) | 0.0 | 0.0 | 0.2 |
| Others (%) | 4.4 | 4.9 | 5.4 |

Comparative Example 2

20 g of a catalyst (fluorine content: about 15.0% by weight) obtained by fluorinating a chromium oxide represented by the composition formula: $CrO_2$ was placed into a tubular Hastelloy reactor with an inner diameter of 15 mm and a length of 1 m. The reaction tube was maintained at atmospheric pressure (0.1 MPa) and 250° C., and anhydrous hydrogen fluoride (HF) gas was supplied to the reactor at a flow rate of 114 mL/min (flow rate at 0° C., 0.1 MPa) for 1 hour. After the flow rate of HF was adjusted to 76 mL/min, $CCl_2=CClCH_2Cl$ (HCO-1230xa) having a water content of 240 ppm was supplied at a flow rate of 3.8 mL/min (gas flow rate at 0° C., 0.1 MPa). The water content in the reaction system at this point based on the weight of HCO-1230xa was 330 ppm. The molar ratio of HF:HCO-1230xa was 20:1, and the contact time ($W/F_0$) was 15.0 g·sec/cc.

The outlet gas from the reactor after 40 hours, 70 hours, and 110 hours was analyzed using gas chromatography. Table 7 shows the analysis results.

Under these conditions, the conversion of HCO-1230xa was 85.2% after 40 hours, and decreased to 50.0% after 110 hours. Additionally, the yield (conversion x selectivity) of HCFO-1233xf was 75.5% after 40 hours, and decreased to 23.0% after 110 hours. Moreover, the total yield of useful compounds of HCFO-1233xf, HFC-2450b, and HFO-1234yf was also decreased at 18.0%/day.

TABLE 7

|  | Reaction Time (hr) | | |
| --- | --- | --- | --- |
|  | 40 | 70 | 110 |
| Conversion of HCO-1230xa (%) | 85.2 | 68.8 | 50.0 |
| Selectivity of HFO-1234yf (%) | 0.0 | 0.0 | 0.0 |
| Selectivity of HFC-245cb (%) | 0.0 | 0.0 | 0.0 |
| Selectivity of HCFO-1233xf (%) | 88.6 | 76.7 | 46.0 |
| Selectivity of HCFO-1232xf (%) | 8.4 | 17.3 | 26.9 |
| Others (%) | 3.0 | 6.0 | 27.1 |

EXAMPLE 6

A reaction was carried out under the same conditions as in Comparative Example 2, except that chlorine gas was supplied at 0.12 mL/min (gas flow rate at 0° C., 0.1 MPa) concurrently with supply of $CCl_2=CClCH_2Cl$ (HCO-1230xa). At this point, the water content in the reaction system based on the weight of HCO-1230xa was 340 ppm, and the molar ratio of $Cl_2$:HCO-1230xa was 0.032:1. Table 8 shows the analysis results of the outlet gas.

Under these conditions, the conversion of HCO-1230xa was maintained at a high value: 92.9% after 25 hours and 84.3% after 100 hours; the yield of HCFO-1233xf was also maintained at a high value: 88.4% after 25 hours, and 78.0% after 100 hours. In addition, the rate of decline in the total yield of useful compounds of HCFO-1233xf, HFC-2450b, and HFO-1234yf was 3.4%/day, and the deterioration of catalytic activity was reduced by the supply of chlorine gas.

TABLE 8

|  | Reaction Time (hr) | | |
| --- | --- | --- | --- |
|  | 25 | 70 | 100 |
| Conversion of HCO-1230xa (%) | 92.9 | 88.0 | 84.3 |
| Selectivity of HFO-1234yf (%) | 0.2 | 0.2 | 0.1 |
| Selectivity of HFC-245cb (%) | 0.3 | 0.2 | 0.2 |
| Selectivity of HCFO-1233xf (%) | 95.2 | 93.7 | 92.6 |
| Selectivity of HCFO-1232xf (%) | 1.8 | 3.0 | 3.8 |
| Others (%) | 2.5 | 2.9 | 3.3 |

The invention claimed is:

1. A process for producing 2-chloro-3,3,3-trifluoropropene, comprising:
    continuously reacting anhydrous hydrogen fluoride with at least one chlorine-containing compound in a gas phase in the presence of a chromium atom-containing fluorination catalyst while heating for at least 200 hours on an industrial scale,
    wherein the at least one chlorine-containing compound is one or more chloropropene(s) of Formula (3): $CXY=CClCH_2A$, wherein X and Y are the same or different and each is F or Cl, and A is a halogen atom, and
        wherein the reaction is carried out in the presence of molecular chlorine, wherein the amount of molecular chlorine is about 0.001 to about 0.3 moles per mole of the at least one chlorine-containing compound,
        wherein the reaction is carried out at a temperature in the range of 200° C. to 300° C., and
        wherein the reaction is carried out at approximately atmospheric pressure or less.

2. The process according to claim 1, wherein the amount of molecular chlorine supplied is 0.001 to 0.2 moles per mole of the at least one chlorine-containing compound.

3. The process according to claim 1, wherein the chromium atom-containing fluorination catalyst is at least one catalyst selected from the group consisting of chromium oxides and fluorinated chromium oxides.

4. The process according to claim 3, wherein the fluorination catalyst is at least one catalyst selected from the group consisting of chromium oxides of the composition formula: $CrO_m$ (1.5<m<3) and fluorinated chromium oxides obtained by fluorinating the chromium oxides.

5. The process according to claim 1, wherein the reaction is carried out using 3 moles or more of anhydrous hydrogen fluoride per mole of the at least one chlorine-containing compound used as a starting material.

6. The process according to claim 1, wherein the at least one chlorine-containing compound used as a starting material is 1,1,2,3-tetrachloropropene.

7. The process according to claim 1, wherein the reaction is carried out with a contact time of about 0.5 to about 70 g. sec/mL.

8. A process for producing 2-chloro-3,3,3-trifluoropropene, comprising:
    continuously reacting anhydrous hydrogen fluoride with at least one chlorine-containing compound in a gas phase in the presence of a chromium atom-containing fluorination catalyst while heating for at least 200 hours on an industrial scale,
    wherein the at least one chlorine-containing compound is one or more chloropropene(s) of Formula (3): $CXY=CClCH_2A$, wherein X and Y are the same or different and each is F or Cl, and A is a halogen atom, and
    wherein the reaction is carried out with a water content in the reaction system of 300 ppm or less based on the total weight of the at least one chlorine-containing compound used as a starting material with the proviso that the water content in the reaction system is not 0 ppm, and
    wherein the reaction is carried out at approximately atmospheric pressure or less.

9. The process according to claim 8, wherein the reaction is carried out with a water content in the reaction system of 100 ppm or less based on the total weight of the at least one chlorine-containing compound used as a starting material.

10. The process according to claim 8, wherein the chromium atom-containing fluorination catalyst is at least one catalyst selected from the group consisting of chromium oxides and fluorinated chromium oxides.

11. The process according to claim 10, wherein the fluorination catalyst is at least one catalyst selected from the group consisting of chromium oxides of the composition formula:
    $CrO_m$ (1.5<m<3) and fluorinated chromium oxides obtained by fluorinating the chromium oxides.

12. The process according to claim 8, wherein the reaction is carried out using 3 moles or more of anhydrous hydrogen fluoride per mole of the at least one chlorine-containing compound used as a starting material.

13. The process according to claim 8, wherein the at least one chlorine-containing compound used as a starting material is 1,1,2,3-tetrachloropropene.

14. A process for producing 2-chloro-3,3,3-trifluoropropene, comprising:
    continuously reacting anhydrous hydrogen fluoride with at least one chlorine-containing compound in a gas phase in the presence of a chromium atom-containing fluorination catalyst while heating for at least 200 hours on an industrial scale,
    wherein the at least one chlorine-containing compound is one or more chloropropene(s) of Formula (3): $CXY=CClCH_2A$, wherein X and Y are the same or different and each is F or Cl, and A is a halogen atom, and
    wherein the reaction is carried out in the presence of molecular chlorine and with a water content in the reaction system of 300 ppm or less based on the total weight of the at least one chlorine-containing compound used as a starting material with the proviso that the water content in the reaction system is not 0 ppm,
    wherein the amount of molecular chlorine is about 0.001 to about 0.3 moles per mole of the at least one chlorine-containing compound, and
    wherein the reaction is carried out at approximately atmospheric pressure or less.

15. The process according to claim 14, wherein the amount of molecular chlorine supplied is 0.001 to 0.2 moles per mole of the at least one chlorine-containing compound.

16. The process according to claim 14, wherein the reaction is carried out with a water content in the reaction system of 100 ppm or less based on the total weight of the at least one chlorine-containing compound used as a starting material.

17. The process according to claim 14, wherein the chromium atom-containing fluorination catalyst is at least one catalyst selected from the group consisting of chromium oxides and fluorinated chromium oxides.

18. The process according to claim 17, wherein the fluorination catalyst is at least one catalyst selected from the group consisting of chromium oxides of the composition formula:

$CrO_m$ (1.5<m<3) and fluorinated chromium oxides obtained by fluorinating the chromium oxides.

19. The process according to claim 14, wherein the reaction is carried out using 3 moles or more of anhydrous hydrogen fluoride per mole of the at least one chlorine-containing compound used as a starting material.

20. The process according to claim 14, wherein the at least one chlorine-containing compound used as a starting material is 1,1,2,3-tetrachloropropene.
   wherein the reaction is carried out at approximately atmospheric pressure or less.

\* \* \* \* \*